United States Patent [19]

Trepanier

[11] 4,002,625
[45] Jan. 11, 1977

[54] SUBSTITUTED 1,2,4-TRIAZINE-3-METHANAMINES

[75] Inventor: Donald L. Trepanier, Midland, Mich.

[73] Assignee: The Dow Chemical Company, Midland, Mich.

[22] Filed: Jan. 26, 1976

[21] Appl. No.: 652,607

[52] U.S. Cl. .............................. 260/248 AS; 71/93; 424/249
[51] Int. Cl.$^2$ ........................................ C07D 253/06
[58] Field of Search .............................. 260/248 AS

[56] References Cited

FOREIGN PATENTS OR APPLICATIONS 847,360  7/1970  Canada .............................. 260/248

Primary Examiner—John M. Ford
Attorney, Agent, or Firm—James W. Ambrosius

[57] ABSTRACT

Novel N-(phenyl)-1,4,5,6-tetrahydro-1,2,4-triazine-3-methanamines are disclosed which are useful as herbicides, insecticides, and antimicrobial agents. Various member compounds are also pharmacologically active.

4 Claims, No Drawings

SUBSTITUTED 1,2,4-TRIAZINE-3-METHANAMINES

SUMMARY OF THE INVENTION

This invention relates to novel N-(phenyl)-1,4,5,6-tetrahydro-1,2,4-triazine-3-methanamines corresponding to the formula:

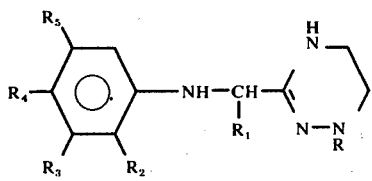

and the addition salts thereof. In the present specification and claims R and $R_1$ independently represent hydrogen or a lower alkyl of from 1 to 3 carbon atoms and $R_2$, $R_3$, $R_4$, and $R_5$ independently represent hydrogen, methyl, trihalomethyl, or a halogen.

Operable addition salts of the above triazine compounds are those having anionic moieties which have no substantial detrimental effects upon the herbicidal, compounds are those having anionic moieties which have no substantial detrimental effects upon the herbicidal, insecticidal, or antimicrobial activity of the compounds. Representative salts include acid addition salts formed by addition to the triazine compounds inorganic acids such as hydrochloric, hydrobromic, sulfuric, and nitric acid or of organic acids such as acetic, lactic, maleic, succinic, fumaric, glutaric, citric, malic, sulfonic, tartaric, and the like.

The compounds of the present invention are crystalline solids which are of varying degrees of solubility in water and various organic solvents such as ether, alcohols, chlorinated hydrocarbons, lower alkanes, and esters. The compounds of the present invention exhibit herbicidal, insecticidal, and antimicrobial activities, however a given compound may not show activity in all of the above-mentioned areas. In addition, some of the compounds are pharmacologically active.

DESCRIPTION OF THE PRIOR ART 1,2,4-Triazines which are related in structure to the compounds of the present invention, but lack the amino linkage to the phenyl group, are disclosed in U.S. Pat. No. 3,471,486. Other 1,2,4-triazines are disclosed in U.S. Pat. Nos. 3,021,328; 3,135,737; 3,426,635; 3,428,635; 3,463,777; 3,471,485; 3,471,487 and 3,471,488. The condensation of β-aminoalkylhydrazines with iminoesters and orthoesters to yield 1,4,5,6-tetrahydro-1,2,4-triazines is disclosed in Trepanier et al., Jour. of Medicinal Chem., 10, 228 (1967).

Herbicidal activity has been shown for 2-alkylthio-4,6-diamino-s-triazine compounds. German Auslegenschriften 141,633.

DETAILED DESCRIPTION OF THE INVENTION

In general compounds of the present invention are prepared by the reaction of a selected N-(cyanomethyl)-aniline with methanol at room temperature in the presence of a catalytic amount of sodium methoxide to yield the phenylaminomethylimidate. See Schaefer et al., J. Org. Chem., 26, 412 (1961). The imidate formed in this manner is caused to react with a 2-aminoethylhydrazine to yield the desired 1,2,4-triazine of the present invention. The two step reaction may be represented as follows:

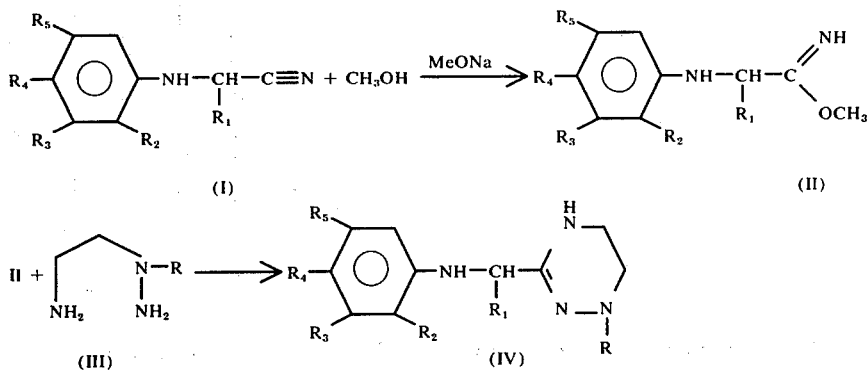

wherein $R_1$, $R_2$, $R_3$, $R_4$ and $R_5$ represent the same substitutions indicated above. If unavailable, N-(cyanomethyl)aniline used as a starting material in (I) above is prepared by reacting a substituted or unsubstituted aniline with a selected aldehyde, sodium hydrogen sulfate, and potassium cyanide. The reaction may be carried out on a steambath.

The following examples illustrate the preparation of compounds that are the subject of the present invention, but are not to be construed as a limitation thereon.

EXAMPLE 1

Preparation of 3-(anilinomethyl)-1,4,5,6-tetrahydro-1-methyl-1,2,4-triazine

To 110 ml. of methyl alcohol 16.5 grams (0.125 mol.) of N-(cyanomethyl)aniline was added along with 0.68 grams (0.0125 mol.) of sodium methoxide as a catalyst. The reaction mixture was stirred at room temperature overnight. The following day 0.75 ml. of acetic acid was added to the mixture. The reaction mixture was evaporated to dryness and the semicrystalline imidate was recovered.

The recovered imidate (17 grams) was added to 100 ml. of anhydrous ethanol and 11.2 grams of 1-(2-aminoethyl)-1-methylhydrazine. This mixture was stirred at room temperature for 2 hours and refluxed overnight. The reaction mixture was cooled and evaporated to yield a gummy solid. Ether (150 ml.) was added and the crystals that formed were filtered off.

The crude 3-(anilinomethyl)-1,4,5,6-tetrahydro-1-methyl-1,2,4-triazine was recrystallized from isopropyl alcohol. The melting point of the product was 124°–125° C.

Elemental analysis gave carbon 64.42%, hydrogen 7.99%, and nitrogen 27.14%. Theoretical calculated is carbon 64.67%, hydrogen 7.89%, and nitrogen 27.42%.

EXAMPLE 2

Preparation of 1,4,5,6-tetrahydro-N-(2-(trifluoromethyl)-phenyl)-1,2,4-triazine-3-methanamine A solution containing 16 grams of N-(cyanomethyl)-2-(trifluoromethyl)aniline in 45 ml. of ethyl alcohol was cooled to about 5° C. To this solution 0.4 grams of sodium methoxide was added. The reaction mixture was stirred for 24 hours. Acetic acid (0.45 ml.) was added to the reaction mixture and it was cooled for 2 hours in ice water.

2-Aminoethylhydrazine was added to the mixture and it was refluxed for 2 hours. The mixture that resulted was diluted with about 150 ml. of benzene and the sodium acetate that separated was filtered off. The filtrate was concentrated by evaporation and about 100 ml. of hexane was added and the mass chilled. Beige crystals of 1,4,5,6-tetrahydro-N-(2-(trifluoromethyl)-phenyl)-1,2,4-triazine-3-methanamine formed. The product was recrystallized from warm benzene to which hexane was added. The product had a melting point of 97°–98° C.

The structure was substantiated by ir, nmr and elemental analyses.

Using the general procedure described above other 1,2,4-triazine-3-methanamines corresponding to the formula

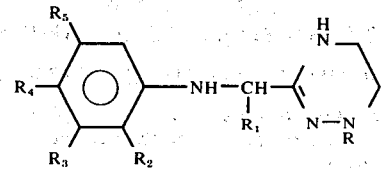

were prepared. These compounds are listed in Table I.

TABLE I

| Compound Example No. | R | $R_1$ | $R_2$ | $R_3$ | $R_4$ | $R_5$ | Recrystallization Solvent | Mp°, C. |
| --- | --- | --- | --- | --- | --- | --- | --- | --- |
| 3 | H | H | $CF_3$ | H | F | H | $C_6H_6$/hexane | 97–98 |
| 4 | $CH_3$ | H | $CF_3$ | H | F | H | $C_6H_6$/hexane | 112–114 |
| 5 | H | H | H | $CF_3$ | F | H | ethanol/$H_2O$ | 156–158 |
| 6 | $CH_3$ | H | H | $CF_3$ | Cl | H | $C_6H_6$/hexane | 149–150 |
| 7 | $CH_3$ | H | $CH_3$ | H | H | H | $C_6H_6$/hexane | 79–80 |
| 8 | H | H | $CH_3$ | H | H | H | $C_6H_6$/hexane | 105–106 |
| 9 | $CH_3$ | $CH_3$ | H | $CF_3$ | H | H | $C_6H_6$/hexane | 126–127 |
| 10 | H | $CH_3$ | H | $CF_3$ | H | H | $C_6H_6$/hexane | 123–124 |
| 11 | H | H | H | $CF_3$ | Cl | H | $CH_3CCl_3$ | 171–172 |
| 12 | $CH_3$ | H | $CF_3$ | H | H | H | $C_6H_6$/hexane | 98–100 |
| 13 | $CH_3$ | H | H | H | $CH_3$ | H | isopropanol/$C_6H_6$ | 126–127 |
| 14 | $CH_3$ | H | H | $CH_3$ | H | H | ethanol/$C_6H_6$ | 87–88 |
| 15 | H | H | H | H | $CH_3$ | H | $C_6H_6$ | 135–136 |
| 16 | H | H | H | $CH_3$ | H | H | $C_6H_6$/hexane | 106–107 |
| 17 | $CH_3$ | H | F | H | F | H | $C_6H_6$/hexane | 81–83 |
| 18 | $CH_3$ | H | F | H | F | H | isopropanol/ethanol | 113–114 |
| 19 | H | H | F | H | H | H | $C_6H_6$/hexane | 104–106 |
| 20 | H | H | F | H | F | H | $C_6H_6$ | 132–133 |
| 21 | H | H | H | H | H | H | $C_6H_6$/hexane | 110–111 |
| 22 | $CH_3$ | H | H | $CF_3$ | H | H | ethyl ether/hexane | 107–108 |
| 23 | H | H | H | $CF_3$ | H | H | ethanol | 165–166 |
| 24 | H | H | F | H | H | F | $C_6H_6$/hexane | 121–122 |
| 25 | $CH_3$ | H | F | H | H | F | $C_6H_6$/hexane | 97–98 |

The compounds of the present invention were tested for use as pre-emergent and as post-emergent herbicides on various selected plant species.

EXAMPLE 26

Use of Compounds as a Pre-emergent Herbicide

An aqueous composition consisting of a predetermined amount of one of the compounds of the present invention was dispersed in water and employed as a pre-emergent herbicide. The compositions were employed to treat separate pots filled to within one inch of the top with a medium-textured soil wherein each pot contained good, viable seeds of one of a predetermined plant species. Each pot was maintained so as to prevent any interaction with test compounds in different pots. Each pot was treated with one of the compositions as a soil drench in sufficient volume to wet the top 1½ to 2 inches of soil. The compositions were applied to the pots so that the respective pots of a given plant species were treated with a different test compound. Another pot was treated only with water to serve as a control. After treatment, the pots were maintained for two weeks under greenhouse conditions conducive for good plant germination and growth and watered as necessary. The specific plant species, test compound, dosage, and results are set forth below in Table II. Numbers in the column below the plant species indicate herbicidal activity and shows the concentration of compound used expressed in terms of pounds/acre.

TABLE II

| Compound Ex. No. | Cotton | Wild Oats | Pig Weeds | Bind Weed | Wild Mustard Charlock | Beans | Yellow Fox Tail |
| --- | --- | --- | --- | --- | --- | --- | --- |
| 5 | 10 | | | | | | |

TABLE II-continued

| Compound Ex. No. | Cotton | Wild Oats | Pig Weeds | Bind Weed | Wild Mustard Charlock | Beans | Yellow Fox Tail |
|---|---|---|---|---|---|---|---|
| 10 | 10 | 10 | | | | | |
| 13 | | | 20 | | | | |
| 18 | | | 20 | 20 | | | |
| 20 | | | 20 | | 20 | 20 | |
| 22 | | | 20 | 20 | 20 | | 20 |
| 23 | | | 20 | 20 | 20 | | |
| 24 | | | | | | 10 | |

EXAMPLE 27

Use of Compounds as a Post-Emergent Herbicide

A series of aqueous compositions each consisting of a predetermined amount of one of the compounds of the present invention dispersed in water were employed as post-emergent herbicides. The respective compositions were employed to treat separate stands of a predetermined plant species grown to a height of 2 to 4 inches in pots containing sandy loam soil. Each pot was maintained so as to prevent any interaction with test compounds in different pots. Each pot was treated with one of the compositions as a spray applied to the plants to run off. The compositions were applied to the pots so that respective pots of a given plant species were treated with one of each of the test compounds. Another pot was treated only with water to serve as a control. After treatment the pots were maintained for two weeks under greenhouse conditions conducive for good plant growth and watered as necessary. The specific plant species, test compounds, dosage, and results are set forth below in Table III. Numbers in the columns under the plant species indicate herbicidal activity and show the concentration of compound used in parts per million.

TABLE III

| Compound Ex. No. | Yellow Fox Tail | Crabgrass | Velvet Leaf | Pig Weeds | Bind Weed | Wild Mustard Charlock | Beans |
|---|---|---|---|---|---|---|---|
| 4 | 4000 | | | | | | |
| 5 | 4000 | 4000 | | | | | |
| 9 | 4000 | 4000 | 4000 | | | | |
| 13 | 4000 | | | 4000 | | | |
| 14 | 4000 | | | 4000 | | | |
| 15 | 4000 | | | | | | |
| 18 | | | | | | 4000 | 4000 |
| 19 | 4000 | | | 4000 | | | |
| 22 | 4000 | 4000 | | 4000 | | 4000 | 4000 |

Various compounds of the present invention have also shown insecticidal activity. Table IV lists compounds having such activity and gives the concentrations at which they were found to be effective in parts per million in an aqueous solution.

Member compounds have also shown antimicrobial activity at concentrations of about 500 parts per million when used against various species such as for example, Bacillus subtilis, Staphylococcus aureus, Salmonella typhosa, Mycobacterium phlei, Trichoderm sp Madison P-42, Escherichia coli, Trichophton mentogrophytes, Pullularia pullulans, and Candida pelliculosa. The following compounds were found to be effective against one or more of the above species.

N-(4-fluoro-3-(trifluoromethyl)-phenyl)-1,4,5,6-tetrahydro-1-methyl-1,2,4-triazine-3-methanamine (Example 4).

N-(4-fluoro-3-(trifluoromethyl)phenyl)-1,4,5,6-tetrahydro-1,2,4-triazine-3-methanamine (Example 5).

N-(4-chloro-3-(trifluoromethyl)phenyl)-1,4,5,6-tetrahydro-1-methyl-1,2,4-triazine-3-methanamine (Example 6).

1,4,5,6-tetrahydro-N-(2-methylphenyl)-1,2,4-triazine-3-methanamine (Example 8).

1,4,5,6-tetrahydro-α-methyl-N-(trifluoromethylphenyl)-1,2,4-triazine-3-methanamine (Example 10).

N-(4-chloro-3-(trifluoromethyl)phenyl)-1,4,5,6-tetrahydro-1,2,4-triazine-3-methanamine (Example 11).

1,4,5,6-tetrahydro-1-methyl-N-2-(trifluoromethylphenyl)-1,2,4-triazine-3-methanamine (Example 12).

1,4,5,6-tetrahydro-N-(4-methylphenyl)-1,2,4-triazine-3-methanamine (Example 15).

1,4,5,6-tetrahydro-N-(3-methylphenyl)-1,2,4-triazine-3-methanamine (Example 16).

TABLE IV

| Compound Ex. No. | Cabbage Looper | Beet Army Worm Larvae | Southern Army Worm | Boll Weevil | Boll Worm | Yellow Fever Mosquito Adult | House Fly | Southern House Mosquito Larvae |
|---|---|---|---|---|---|---|---|---|
| 1 | 400 | | | | | | | |
| 6 | | 400 | | | | | | |
| 10 | 400 | | | | | | | |
| 23 | | | 500 | 500 | 400 | 10.0 | | |
| 24 | | | | | | | 500 | |
| 25 | | | | | | | 500 | 1.00 |

N-(2-fluorophenyl)-1,4,5,6-tetrahydro-1,2,4-triazine-3-methanamine (Example 19).

N-(2,4-difluorophenyl)-1,4,5,6-tetrahydro-1,2,4-triazine-3-methanamine (Example 20).

N-(2,5-difluorophenyl)-1,4,5,6-tetrahydro-1,2,4-triazine-3-methanamine (Example 24).

Some of the compounds also display various pharmacological activity. For instance the compounds of Example 2 and Example 7 have been shown to enhance learning and memory in mice by increasing the ability of mice fed on diets containing 0.125% of these compounds to avoid electric shocks.

The compound of Example 3 has been shown to prevent the formation of clots in rabbit serum that has been sensitized to the split products of mouse fibrin. The compounds therefore have demonstrated thromolysis activity and are useful in the treatment of various conditions that cause clots to form within the vascular system of a mammal.

Central Nervous System stimulant and antidepressant activity has been recognized in several member compounds as for example, compounds Examples 16 and 21. Mice injected with about 60 mg/kg body weight of these compounds have been shown to be protected against reserpine induced ptosis. In addition, compounds Examples 17 and 21 have been shown to be effective in the treatment of hypertension in rats when administered orally at a dosage of 30 mg/kg of body weight.

I claim:
1. A compound of the formula

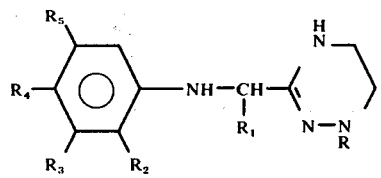

and the addition salts thereof, wherein R and $R_1$ independently represent hydrogen or a lower alkyl of from 1 to 3 carbon atoms and $R_2$, $R_3$, $R_4$, and $R_5$ independently represent hydrogen, methyl, trihalomethyl, or a halogen.

2. The compound of claim 1 wherein R is hydrogen and $R_1$ is hydrogen.

3. The compound of claim 1 wherein R is methyl and $R_1$ is hydrogen.

4. The compound of claim 1 wherein $R_1$ and $R_5$ is hydrogen and $R_2$, $R_3$, and $R_4$ independently represent trifluoromethyl, methyl, fluorine, chlorine, or hydrogen.

* * * * *

UNITED STATES PATENT AND TRADEMARK OFFICE
CERTIFICATE OF CORRECTION

PATENT NO. : 4,002,625

DATED : January 11, 1977

INVENTOR(S) : Donald L. Trepanier

Page 1 of 2

It is certified that error appears in the above-identified patent and that said Letters Patent are hereby corrected as shown below:

Column 4, line 5, should read

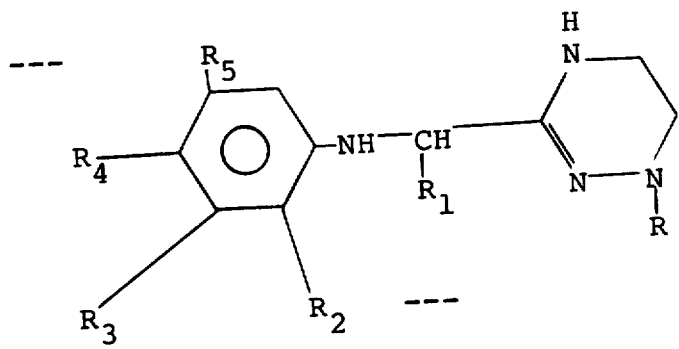

Column 8, line 10, should read

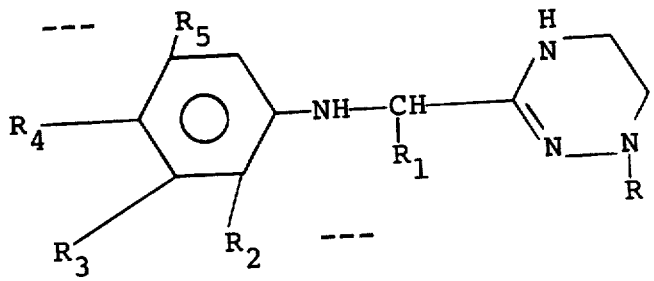

continued

UNITED STATES PATENT AND TRADEMARK OFFICE
CERTIFICATE OF CORRECTION

PATENT NO. : 4,002,625

DATED : January 11, 1977

Page 2 of 2

INVENTOR(S) : Donald L. Trepanier

It is certified that error appears in the above-identified patent and that said Letters Patent are hereby corrected as shown below:

Column 4, line 26, compound Example No. 17, should read

-- 17   $CH_3$   H   F   H   H   H   $C_6H_6$/hexane   81-83 --

Signed and Sealed this

Fourteenth Day of June 1977

[SEAL]

Attest:

RUTH C. MASON
*Attesting Officer*

C. MARSHALL DANN
*Commissioner of Patents and Trademarks*